(12) United States Patent
Contreras Rojas et al.

(10) Patent No.: US 12,566,166 B2
(45) Date of Patent: Mar. 3, 2026

(54) MINERALOGICAL ANALYSIS SYSTEM OF COPPER CONCENTRATE

(71) Applicant: CODELCOTEC SPA, Santiago (CL)

(72) Inventors: Leonel Contreras Rojas, Santiago (CL); Víctor Duarte Olave, Santiago (CL); Eduardo Rodríguez Seguel, Santiago (CL); Patricio Lara Torres, Santiago (CL)

(73) Assignee: CODELCOTEC SPA, Santiago (CL)

( * ) Notice: Subject to any disclaimer, the term of this patent is extended or adjusted under 35 U.S.C. 154(b) by 349 days.

(21) Appl. No.: 17/788,839

(22) PCT Filed: Dec. 4, 2020

(86) PCT No.: PCT/CL2020/050168
§ 371 (c)(1),
(2) Date: Jun. 24, 2022

(87) PCT Pub. No.: WO2021/127795
PCT Pub. Date: Jul. 1, 2021

(65) Prior Publication Data
US 2023/0033441 A1 Feb. 2, 2023

(30) Foreign Application Priority Data
Dec. 27, 2019 (CN) .......................... 201911374162.0

(51) Int. Cl.
*G01N 33/202* (2019.01)
*C22B 15/00* (2006.01)
(Continued)

(52) U.S. Cl.
CPC ......... *G01N 33/202* (2019.01); *C22B 15/003* (2013.01); *C22B 15/0041* (2013.01);
(Continued)

(58) Field of Classification Search
None
See application file for complete search history.

(56) References Cited

U.S. PATENT DOCUMENTS 4,149,945 A     4/1979  Kust
6,735,278 B2 *  5/2004  Madsen  ............... G01N 33/383
378/71
(Continued)

FOREIGN PATENT DOCUMENTS

WO     2011089622 A2     7/2011

OTHER PUBLICATIONS

May 12, 2021—(WO) International Search Report and Written Opinion—App PCT/CL2020/050168.

*Primary Examiner* — Thomas R Artman
(74) *Attorney, Agent, or Firm* — LUCAS & MERCANTI, LLP

(57) ABSTRACT

This invention patent application addresses a system for the detection and quantification of mineralogical species via x-ray diffraction (XRD) of the concentrate of dry copper before it is injected into a converter or melting furnace. Specifically, it addresses a device that performs a mineralogical analysis, in line and in real time, of the concentrate of copper in the bath smelting furnace via x-ray diffraction (XRD), which allows for control over the ideal mixture for the optimal process for copper sulfide (Cu2S)-white metal, iron sulfide (FeS)-Slag and pyritic sulfur (S2)-temperature.

7 Claims, 6 Drawing Sheets

Proposed system
(can be separated)

(51) Int. Cl.
    *C22B 15/06*         (2006.01)
    *G01N 23/20008*     (2018.01)
    *G01N 23/207*       (2018.01)

(52) U.S. Cl.
    CPC ... *C22B 15/0095* (2013.01); *G01N 23/20008*
        (2013.01); *G01N 23/207* (2013.01); *G01N*
          *2223/056* (2013.01); *G01N 2223/1016*
        (2013.01); *G01N 2223/307* (2013.01); *G01N*
          *2223/616* (2013.01); *G01N 2223/635*
                            (2013.01)

(56)             References Cited

U.S. PATENT DOCUMENTS

| | | | |
|---|---|---|---|
| 8,311,183 B2 * | 11/2012 | O'Dwyer | G01N 23/20091 |
| | | | 378/70 |
| 10,081,849 B2 * | 9/2018 | Chaiko | C22B 15/0063 |
| 10,174,403 B2 * | 1/2019 | Mostaghel | C01B 13/34 |
| 2002/0094060 A1 | 7/2002 | Madsen et al. | |
| 2010/0303206 A1 | 12/2010 | O'Dwyer et al. | |
| 2017/0226611 A1 | 8/2017 | Chaiko et al. | |
| 2017/0362680 A1 | 12/2017 | Mostaghel et al. | |
| 2023/0003450 A1 * | 1/2023 | Claudio | G01N 23/20 |
| 2023/0033441 A1 * | 2/2023 | Contreras Rojas | G01N 23/207 |

\* cited by examiner

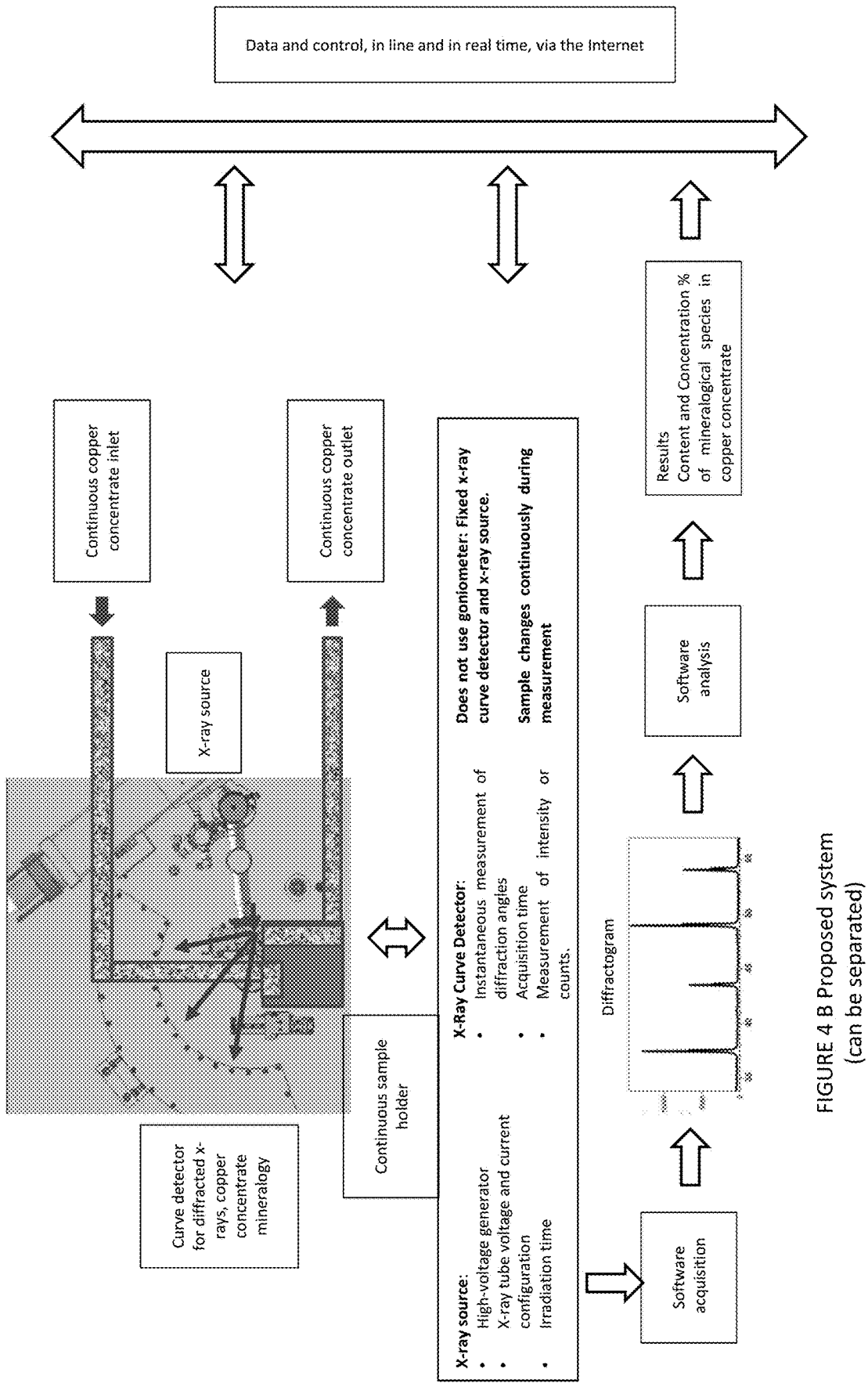
FIGURE 4 B Proposed system
(can be separated)

MINERALOGICAL ANALYSIS SYSTEM OF COPPER CONCENTRATE

CROSS-REFERENCE TO RELATED APPLICATIONS

The present application is a U.S. National Stage application under 35 U.S.C. § 371 of International Application PCT/CL2020/050168 (published as WO/2021/127795), filed Dec. 4, 2020, which claims the benefit of priority to Application CN 201911374162.0, filed Dec. 27, 2019. Benefit of the filing date of these prior applications is hereby claimed. Each of these prior applications is hereby incorporated by reference in its entirety.

This invention patent application addresses a system for the detection and quantification of mineralogical species via x-ray diffraction (XRD) of the concentrate of dry copper before it is injected into a converter or melting furnace. Specifically, it addresses a device that performs a mineralogical analysis, in line and in real time, of the concentrate of copper in the bath smelting furnace via x-ray diffraction (XRD), which allows for control over the ideal mixture for the optimal process for copper sulfide (Cu2S)-white metal, iron sulfide (FeS)-Slag and pyritic sulfur (S2)-temperature.

BACKGROUND

Understanding the quality and quantity of the minerals found in the dry concentrate material prior to it being placed in a melting furnace is fundamental in order to correctly and efficiently carry out the conversion operation. Currently, all foundries take a sample of the dry copper concentrate every so often prior to placing said concentrate in the furnace. The aforementioned sample is taken to a laboratory and submitted to x-ray fluorescence. This is an elemental analysis technique that shows the percentage of Cu, Fe and S present in the sample. The mineralogy is determined by mass-balance and stoichiometry.

Mineralogy measurements with XRD are performed sporadically, since the sample is taken to a laboratory and divided in order to have a representative sample that does not exceed the 10 g of the total sample extruded. In general, the process of obtaining a result is slow, considering the natural operation time of the furnace. When the plant operator receives a result, a lot of copper concentrate could have gone through. Therefore, the measurement is neither timely nor representative.

The closest thing to this invention is the solution described in patent registration CL42.629, which addresses an in-line measurement and analysis system for mineral concentration to determine the composition of the minerals, the grain size or degree of milling, the type of sulfide associations and the degree of release thereof. This is done via a flotation process that includes a measurement chamber made up of a stainless-steel tube positioned perpendicularly in the center of a goniometer placed on a horizontal platform. On one side of said measurement chamber, an x-ray emitter tube is placed and on the other side, a detector for said x-rays is placed. Both the emitter tube and the detector are on the same plane defined by said horizontal platform. The measurement chamber includes a window parallel to its longitudinal axis and a gate positioned in front of said window that closes it. Both the gate and the window have an opening, 20 mm in diameter, through which the flow sample of pulp passes from a mineral concentration plant in a flotation process. Said flow of pulp is produced bottom-up according to the direction of the longitudinal axis defined by said steel tube. Over said opening, x-rays are introduced from the emitter tube to then be received by said detector. Said opening is sealed with a thin transparent material to avoid the leakage of said flow of pulp through the window. To hold said transparent material, there are two cylinders, one on each side, staggered behind with respect to said measurement chamber, so that one of these two cylinders is loaded with said transparent material and the other cylinder winds as it is used.

The difference with respect to this invention is very clear, insofar as in registration CL42.629, measurement is occurring with the pulp with the concentrate that comes out of the flotation process, prior to the concentrate being submitting to drying, and the proportions of which change once it is dry. Thus, understanding its true quality and quantity in real time, before it enters the furnace, is a matter that is not resolved in the slightest by the registration of reference.

Additionally, the publication of patent US2002094060 describes a method and apparatus to continuously submit a sample from a stream of particulate matter containing crystalline substances and effectively and continuously analyze the sample via x-ray diffraction. A flow of extracted sample feeds onto a continuously moving carrier and its surface is smoothed and flattened to detect and analyze the x-ray diffraction patterns, in order to provide a composition analysis for the crystalline substances. The sample is continuously extracted from the carrier before another sample is fed onto the carrier. The invention is specifically applicable to the analysis of the composition of the cement and cement clinker phases and provides an analysis that is effectively continuous, essentially in real time, in contrast to the laboratory analyses of the aforementioned technique involving discrete samples.

Unlike this invention, the aforementioned publication addresses a technical field that differs from that of this invention (cement industry) and does not describe that the system may be designed to be installed before the inlet to a melting furnace to determine the quality and quantity of the minerals present in the concentrate to be smelted, nor that it is constantly taking samples.

Thus, there is the need for a solution that allows for the detection and quantification of the mineralogical species of the dry copper concentrate before it is injected into smelting furnace (like "E1 Teniente Converter") and that is also capable of performing mineralogical analyses, in line and in real time, of the copper concentrate in a bath smelting furnace.

DETAILED DESCRIPTION OF THE INVENTION

Figure 1:
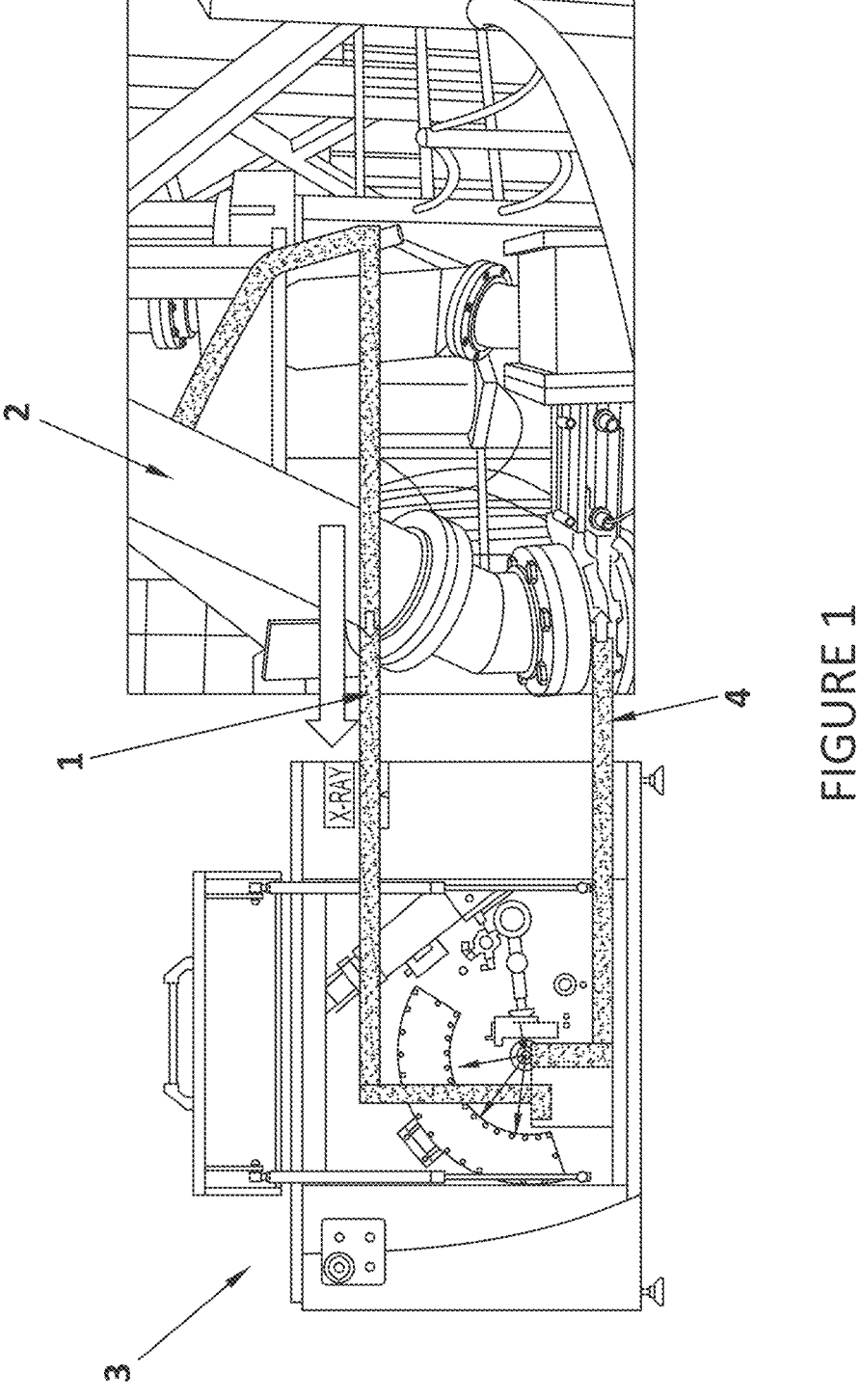
FIG. 1: represents an illustrative diagram of how the x-ray diffractor that forms part of the invention's system will be installed.
Figure 2:
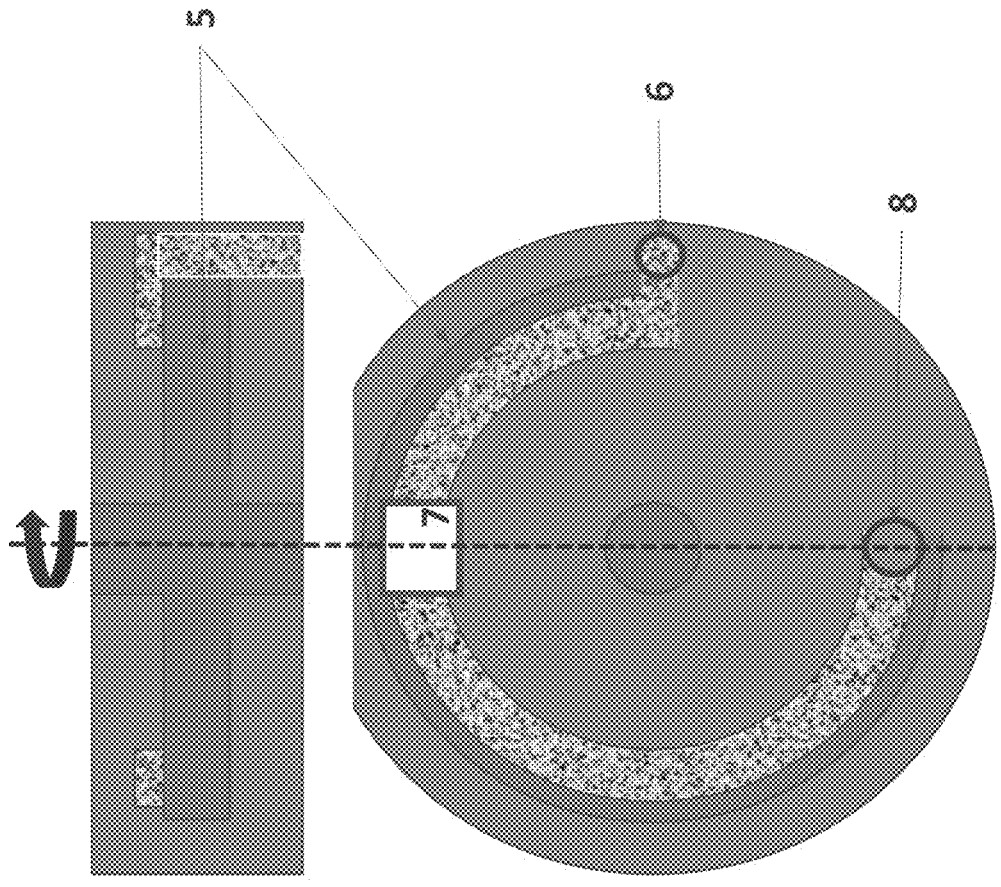
FIG. 2: represents a floor plan illustration of the transport of the concentrate sample within the x-ray diffractor equipment that forms part of the invention's system.

The invention's system is composed of an inlet bypass (1) located in the tube that injects (2) dry concentrate into a bath smelting furnace. The inlet bypass (1) is connected to the x-ray diffraction equipment (3), via which an extracted sample flows from said injection tube (2). From the x-ray diffraction equipment (3), there is a return bypass (4) connected to the injection tube (2), which allows the sample that has been irradiated by the x-ray diffractor (3) to return to the normal injection flow towards the melting furnace. It could also be deposited in a container to later be integrated into the production line manually.

Figure 4:
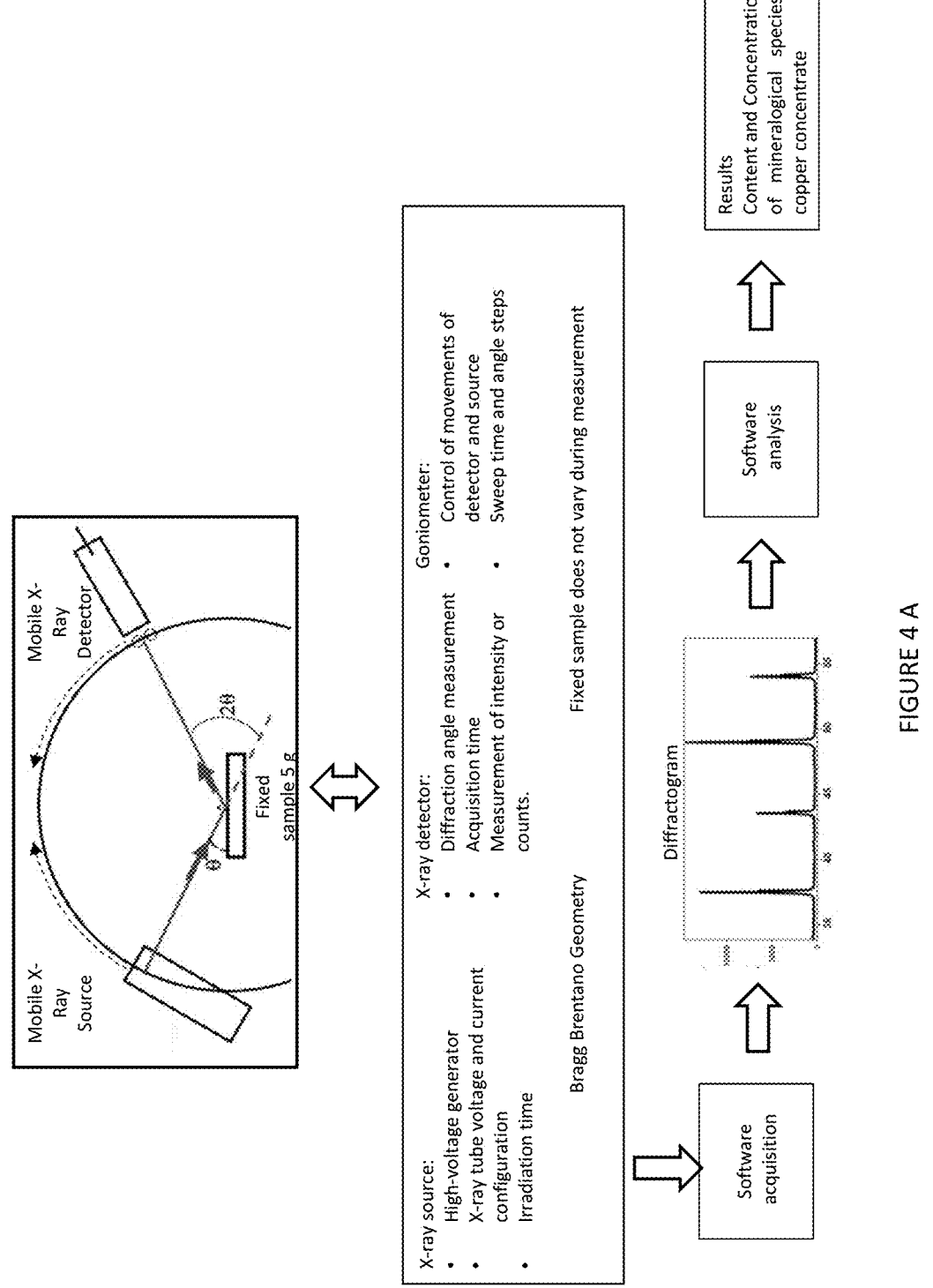
FIGS. 4A-4B: represents a diagram of the operation of standard XRD equipment.

The system is comprised of an inlet valve located next to the inlet bypass (1) that is activated when desired in order for a fraction of the dry concentrate flowing via the injection tube (2) to be diverted toward the x-ray diffraction equipment (3) for sampling. It will be controlled remotely and will provide data in line. In one or more embodiments, as illustrated in FIG. 4A, an X-ray source, and X-ray detector, and a goniometer that controls movements of the detector and source and sweep time and angle steps are used. In one or more embodiments, as illustrated in FIG. 4B, an X-ray source and an X-ray curve detector are used without use of a goniometer. The system operates within a time range for taking samples of between 5 and 20 minutes. Preferably, it is expected to provide a measurement every 15 minutes. The low analysis times are due to the diffractometer technology, with a curved sensor and no moving parts. This imply that the system only take an instantly diffractogram, and consequently this step induce a less time of measurement. Also, this type of technology decreases the probability of failure. The copper concentrate sample to be measured passes continuously through the x-ray diffraction equipment (3) via the inlet bypass (1), for which the inlet valve is activated, which is controlled in an automated manner. This ensures the representativeness of the sample.

Figure 5:
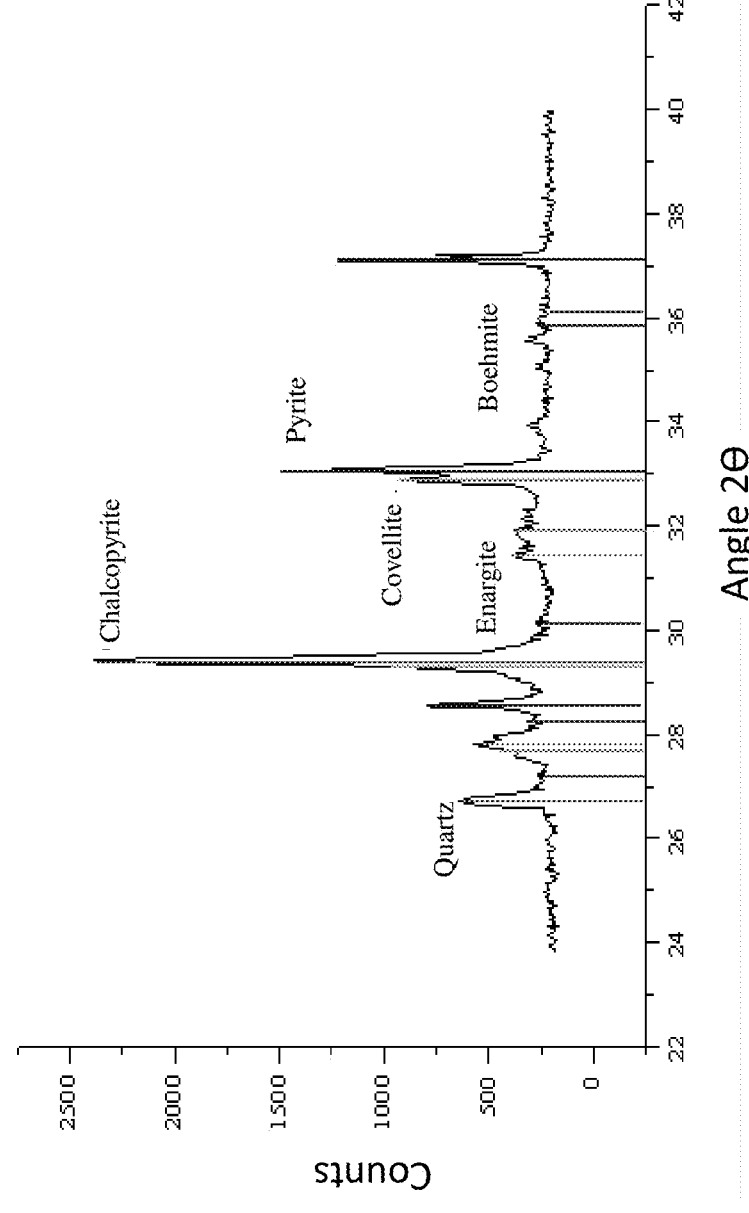
FIG. 5: represents a diffractogram corresponding to a graphic with the angles produced by diffraction that identify the mineral and the height of the intensity peaks or counts related to the number of times it was detected.

The data provided is the relevant mineralogy (chalcopyrite, pyrite, etc.) present in the sample and its concentration, as illustrated in FIG. 5. In addition, said data is used to create a graph of time variations, both for the species present and their concentrations.

The x-ray diffraction equipment (3) chosen to form part of the system has a turntable (5) in which the inlet area (6) for the sample is adjacent to the inlet bypass (1). When the turntable turns (5), the sample passes through the diffraction area (7), where it is irradiated and continues its path toward the outlet area (8) for the sample, which is adjacent to the outlet bypass (4). The equipment can also be comprised of a closed tube of material that is transparent or semi-transparent to x-rays (Kapton, ABS, aluminum, glass or other).

The estimation of the quantity of dry concentrate that is submitted to sampling is defined by the radius of the circle that limits the area of the copper concentrate that is exposed to x-rays or the diffraction area (7) of the sample: (a-b)/2. Thickness of the copper concentrate sample exposed to x-rays: h.

Volume of the copper concentrate sample exposed to x-rays ($V_E$):

$$V_E = \frac{\pi h (a-b)^2}{4}$$

For example, if the diameter of the sample holder unit of the x-ray diffraction equipment (3) is 14 [mm] and the thickness of the sample is 0.5 [mm], each sample holder of the multiple-sample system (30 samples) will have a diameter of 8 [mm] and a thickness of 0.3 [mm].

If a=5 [cm], b=3.6 [cm] (a−b=1.4 [cm] sample holder unit diameter) and h=0.1 [cm]. Then: $V_E$=0.15394 [cc]

Density of the dry copper concentrate injected into the CT: Average=1.9 [g/cc] Range: 1.2 to 2.2 [g/cc]

Then the mass exposed to x-rays: $M_E$=0.2925 [g]

Assuming that in two seconds, the mass of the copper concentrate sample submitted to x-rays completely changes, then in 15 minutes, the mass exposed to x-rays will be: 131.6 [g]. That is to say, it will have a diffractogram with a mass that is much greater than the typical measurement of 45 [min].

Mass measured per day (24 [h]): 12.64 [kg]

Mass measured per month: 379.2 [kg]

The invention's system also includes a standard data computer connected to the x-ray diffraction equipment, which allows a reading to be taken from the equipment and the required mineralogical data to be interpreted. To perform the measurement, it is necessary to understand that x-ray diffraction is the only technique that allows for the detection and quantification of mineralogical species. At an atomic level, it defines the crystalline structures or planes of the minerals that are unique to each species. X-rays are used because their wavelengths (X) allow the crystalline structures to diffract the x-rays (FIG. 3).

Figure 3:
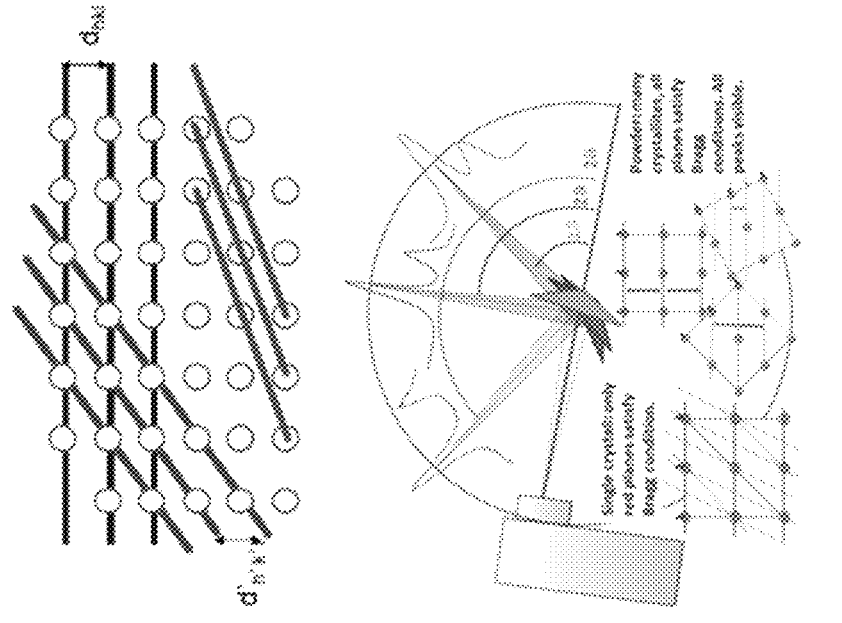
FIG. 3: represents an illustration that explains the concept of mineralogical measurement via x-ray.

As can be observed in FIG. 3, the value of λ is fixed and determined by the anode or anticathode of the x-ray tube chosen. The value of "d" is determined by the mineral content of the sample and the angle of diffraction θ is the variable measured. Bragg's law relates variables λ, d and θ. The clay ring (9) by the source and the detector for the detection of angles according to Bragg Brentano's law of geometry.

When the mineral sample is irradiated with [x-]drays, said rays are diffracted, changing their direction of propagation at angles distinct to each species. Using specialized software installed in the standard data computer, which and how many species are present can be distinguished.

The invention claimed is:

1. A system for detection and quantification of mineralogical species via x-ray diffraction (XRD) of a concentrate of dry copper before injection of the concentrate of dry copper into a converter or melting furnace, the system comprising:

an injection tube adapted to inject dry copper concentrate into a bath smelting furnace;

an inlet bypass having a first end and a second end, the first end located in the injection tube, the inlet bypass adapted to divert a sample of the dry copper concentrate from the injection tube;

an x-ray diffraction equipment connected to the second end of the inlet bypass, the x-ray diffraction equipment adapted to receive the sample of the dry copper concentrate, perform x-ray diffraction on the sample, and perform a mineralogical analysis of the sample;

a return bypass having a third end connected to the x-ray diffraction equipment and a fourth end connected to the injection tube, the return bypass adapted to allow the sample of the dry copper concentrate from the x-ray diffractor to return to an injection flow in the injection tube towards the bath smelting furnace, wherein a volume ($V_E$) of the sample exposed to X-rays is determined according to a relationship as follows:

$$V_E = \frac{\pi h(a-b)^2}{4},$$

wherein:

$V_E$ is a volume of the sample exposed to X-rays;

a is an outer diameter of the sample in the sample holder;

b is an inner diameter of the sample in the sample holder; and h is a thickness of the sample, wherein the x-ray diffraction equipment comprises a curved sensor, and wherein the system is further adapted to divert and perform a mineralogical analysis of a plurality of samples of the dry copper concentrate, wherein the system is adapted to perform a first diversion of a first sample from the injection tube and a second inversion of a second sample from the injection tube with a time between the first and second diversions being between 5-20 minutes.

2. The system for detection and quantification of mineralogical species via x-ray diffraction (XRD) of a concentrate of dry copper in accordance with claim 1, further comprising an inlet valve adapted to allow the sample activated from the injection tube to enter the x-ray diffraction equipment.

3. The system for detection and quantification of mineralogical species via x-ray diffraction (XRD) of a concentrate of dry copper in accordance with claim 1, wherein the x-ray diffraction equipment includes a turntable or confined line comprising a material that is transparent to x-rays and an inlet area for the sample, wherein the inlet area is adjacent to the second end of the inlet bypass.

4. The system for the detection and quantification of mineralogical species via x-ray diffraction (XRD) of a concentrate of dry copper in accordance with claim 3, wherein the x-ray diffraction equipment includes a diffraction area where the sample is irradiated.

5. The system for the detection and quantification of mineralogical species via x-ray diffraction (XRD) of a concentrate of dry copper in accordance with claim 1, wherein the x-ray diffraction equipment includes an outlet area for the sample, whereby the outlet area is adjacent to the outlet bypass.

6. The system for the detection and quantification of mineralogical species via x-ray diffraction (XRD) of a concentrate of dry copper in accordance with claim 1, further comprising a data computer connected to the x-ray diffraction equipment.

7. A system for detection and quantification of mineralogical species via x-ray diffraction (XRD) of a concentrate of dry copper before injection of the concentrate of dry copper into a converter or melting furnace, the system comprising:

an injection tube that injects dry copper concentrate into a bath smelting furnace;

an inlet bypass having a first end and a second end, the first end located in the injection tube, the inlet bypass adapted to divert a sample of the dry copper concentrate from the injection tube;

an x-ray diffraction equipment connected to the second end of the inlet bypass, the x-ray diffraction equipment adapted to receive the sample, perform x-ray diffraction on the sample, and perform a mineralogical analysis of the sample;

a return bypass having a third end connected to the x-ray diffraction equipment and a fourth end connected to the injection tube, the return bypass adapted to allow the sample from the x-ray diffractor to return to an injection flow in the injection tube towards the bath smelting furnace, wherein a volume ($V_E$) of the sample exposed to X-rays is determined according to a relationship as follows:

$$V_E = \frac{\pi h(a-b)^2}{4},$$

wherein:

$V_E$ is a volume of the sample exposed to X-rays;

a is an outer diameter of the sample in the sample holder;

b is an inner diameter of the sample in the sample holder; and h is a thickness of the sample, wherein the x-ray diffraction equipment comprises a sensor comprising a goniometer for controlling movements of detector and source as well as sweep time and angle steps.

\* \* \* \* \*